US009216402B2

(12) United States Patent (10) Patent No.: US 9,216,402 B2
Hassan et al. (45) Date of Patent: Dec. 22, 2015

(54) REACTOR AND CATALYST FOR CONVERTING NATURAL GAS TO ORGANIC COMPOUNDS

(71) Applicant: H R D Corporation, Sugar Land, TX (US)

(72) Inventors: Abbas Hassan, Sugar Land, TX (US);
Aziz Hassan, Sugar Land, TX (US);
Rayford G. Anthony, College Station, TX (US); Gregory G. Borsinger, Chatham, NJ (US)

(73) Assignee: H R D Corporation, Houston, TX (US)

( * ) Notice: Subject to any disclaimer, the term of this patent is extended or adjusted under 35 U.S.C. 154(b) by 157 days.

(21) Appl. No.: 14/071,335

(22) Filed: Nov. 4, 2013

(65) Prior Publication Data

US 2014/0128485 A1 May 8, 2014

Related U.S. Application Data

(60) Provisional application No. 61/723,228, filed on Nov. 6, 2012.

(51) Int. Cl.
*C07C 27/00* (2006.01)
*B01J 19/24* (2006.01)
(Continued)

(52) U.S. Cl.
CPC .............. *B01J 19/2415* (2013.01); *C07C 2/84* (2013.01); *C07C 29/1518* (2013.01); *C07C 2521/06* (2013.01); *C07C 2523/02* (2013.01); *C07C 2523/30* (2013.01); *C07C 2523/75* (2013.01)

(58) Field of Classification Search
CPC ........ C07C 11/04; C07C 31/04; C10G 50/00; C01B 2203/062; C01B 2203/0233; C01B 2203/1241
USPC ................................... 585/658, 654; 518/700
See application file for complete search history.

(56) References Cited

U.S. PATENT DOCUMENTS 2,750,261 A 6/1956 Vladimir et al.
3,205,182 A 9/1965 Padovani et al.
3,351,566 A 11/1967 Taylor et al.
(Continued)

FOREIGN PATENT DOCUMENTS

BE 841812 11/1976
EP 0893183 1/1999
(Continued)

OTHER PUBLICATIONS

Lida et al, Japanese abstract JP 02212437, Aug. 1990.*
(Continued)

*Primary Examiner* — Jafar Parsa
(74) *Attorney, Agent, or Firm* — Timothy S. Westby; Porter Hedges LLP

(57) ABSTRACT

Herein disclosed is a reactor comprising a housing; an inlet tube having a section with perforations along its length, wherein the inlet tube section is within the reactor housing; an outlet tube having a section with perforations along its length, wherein the outlet tube section is within the reactor housing; and at least one cylinder made of sintered metal contained within the reactor housing, wherein the sintered metal is catalytically active. In some cases, the sintered metal in the reactor comprises a porous metallic multifunctional (PMM) catalyst. Other reactor designs and the method of use are also described herein.

9 Claims, 6 Drawing Sheets

(51) Int. Cl.
C07C 2/84 (2006.01)
C07C 29/151 (2006.01)

(56) References Cited

U.S. PATENT DOCUMENTS

| | | | |
|---|---|---|---|
| 3,417,029 | A | 12/1968 | McMahon |
| 3,697,445 | A | 10/1972 | Carter |
| 3,859,370 | A | 1/1975 | Carter et al. |
| 3,868,332 | A | 2/1975 | Carter et al. |
| 3,887,167 | A | 6/1975 | Irwin |
| 4,073,999 | A | 2/1978 | Bryan et al. |
| 4,088,603 | A | 5/1978 | Carter et al. |
| 4,263,173 | A | 4/1981 | Carter et al. |
| 4,409,131 | A | 10/1983 | Fetchin |
| 4,826,796 | A | 5/1989 | Erekson et al. |
| 4,863,712 | A | 9/1989 | Twigg et al. |
| 4,935,572 | A | 6/1990 | Erekson et al. |
| 4,945,078 | A | 7/1990 | Erekson et al. |
| 4,956,327 | A | 9/1990 | Erekson et al. |
| 5,066,629 | A | 11/1991 | Lukey et al. |
| 5,097,086 | A | 3/1992 | Lee et al. |
| 5,118,654 | A | 6/1992 | Choudhary et al. |
| 5,132,481 | A | 7/1992 | Do et al. |
| 5,132,482 | A | 7/1992 | Smith et al. |
| 5,227,342 | A | 7/1993 | Anderson et al. |
| 5,321,185 | A | 6/1994 | Van Der Vaart |
| 5,538,191 | A | 7/1996 | Holl |
| 5,599,510 | A | 2/1997 | Kaminsky et al. |
| 5,736,107 | A | 4/1998 | Inomata et al. |
| 5,849,973 | A | 12/1998 | Van Der Vaart |
| 5,855,815 | A | 1/1999 | Park et al. |
| 5,877,350 | A | 3/1999 | Langer et al. |
| 5,877,387 | A | 3/1999 | Park et al. |
| 5,911,964 | A | 6/1999 | Iwanami et al. |
| 5,936,106 | A * | 8/1999 | Asher et al. ............... 554/98 |
| 6,096,934 | A | 8/2000 | Rekoske |
| 6,355,589 | B1 | 3/2002 | Autenrieth et al. |
| 6,368,366 | B1 | 4/2002 | Langer et al. |
| 6,368,367 | B1 | 4/2002 | Langer et al. |
| 6,383,237 | B1 | 5/2002 | Langer et al. |
| 6,530,964 | B2 | 3/2003 | Langer et al. |
| 6,742,774 | B2 | 6/2004 | Holl |
| 6,752,529 | B2 | 6/2004 | Holl |
| 6,806,087 | B2 | 10/2004 | Kibby et al. |
| 7,165,881 | B2 | 1/2007 | Holl |
| 7,232,848 | B2 | 6/2007 | Mohedas et al. |
| 7,250,543 | B2 | 7/2007 | Bagherzadeh et al. |
| 7,252,692 | B2 | 8/2007 | Rei |
| 7,291,321 | B2 | 11/2007 | Bagherzadeh et al. |
| 7,470,648 | B2 | 12/2008 | Wang et al. |
| 7,538,237 | B2 | 5/2009 | Holl |
| 7,569,511 | B2 | 8/2009 | Castellano et al. |
| 7,588,740 | B1 | 9/2009 | Guarino et al. |
| 7,670,987 | B2 | 3/2010 | Kawashima et al. |
| 7,687,050 | B2 | 3/2010 | Rojey et al. |
| 7,687,051 | B2 | 3/2010 | Hagemeyer et al. |
| 2003/0194362 | A1 | 10/2003 | Rogers et al. |
| 2007/0149392 | A1 | 6/2007 | Ku et al. |
| 2009/0270567 | A1* | 10/2009 | Small et al. ............... 526/64 |
| 2010/0200810 | A1 | 8/2010 | Schmidt et al. |
| 2010/0307726 | A1 | 12/2010 | Chiu et al. |
| 2011/0047864 | A1 | 3/2011 | Bhan et al. |
| 2011/0160314 | A1 | 6/2011 | Schrauwen |

FOREIGN PATENT DOCUMENTS

| | | |
|---|---|---|
| EP | 1584603 | 10/2005 |
| GB | 1220105 | 1/1971 |
| WO | 2002064708 A2 | 8/2002 |

OTHER PUBLICATIONS

Office Action dated Jun. 3, 2011 for U.S. Appl. No. 12/568,280 (16 pgs.).
Office Action dated Jun. 2, 2011 for U.S. Appl. No. 12/427,286 (12 pgs.).
Office Action dated Jun. 25, 2009 for U.S. Appl. No. 12/142,447 (10 pgs.).
Office Action dated Jan. 7, 2010 for U.S. Appl. No. 12/142,447 (6 pgs.).
Office Action dated May 13, 2010 for U.S. Appl. No. 12/142,447 (5 pgs.).
Office Action dated Feb. 4, 2010 for U.S. Appl. No. 12/492,721 (5 pgs.).
Office Action dated Feb. 18, 2010 for U.S. Appl. No. 12/635,433 (6 pgs.).
Office Action dated Feb. 18, 2010 for U.S. Appl. No. 12/635,454 (6 pgs.).
Office Action dated May 14, 2010 for U.S. Appl. No. 12/137,441 (15 pgs.).
Office Action dated Feb. 19, 2010 for U.S. Appl. No. 12/144,459 (10 pgs.).
Office Action dated Sep. 2, 2009 for U.S. Appl. No. 12/142,433 (11 pgs.).
Office Action dated Jan. 29, 2010 for U.S. Appl. No. 12/142,433 (8 pgs.).
Office Action dated May 24, 2011 for U.S. Appl. No. 12/142,433 (10 pgs.).
Office Action dated Apr. 30, 2010 for U.S. Appl. No. 12/141,191 (12 pgs.).
Office Action dated Oct. 27, 2009 for U.S. Appl. No. 12/142,120 (15 pgs.).
Office Action dated May 5, 2010 for U.S. Appl. No. 12/571,537 (12 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
Search Report and Written Opinion dated Jan. 13, 2014 for International Application No. PCT/US2013/068326 (12 pgs.).
IKA-Rotor-Stator Generators—2003 Processing Catalog (38 pgs.).
Gogate, et al. "Cavitation: A technology on the horizon," Current Science 91, No. 1, Jul. 2006, pp. 35-46 (12 pgs.).
IKA, "Introduction to IKA's Three Stage Dispax Reactor," Retrieved from <http://www.ikausa.com/pdfs/process/dr%202000-Homogenizing-Dispersing-Suspending-Emulsifying.pdf> on Aug. 22, 2012 (12 pgs.).
IKA-DRS Reactors website http://www.ikausa.com/dr.him, on Sep. 8, 2010 (2 pgs.).
Burghgraef, et al., "Methane Activation and Dehydrogenation on Nickel and Cobalt: a Computational Study," Surface Science, vol. 324, dated 1995, pp. 345-356 (12 pgs.).
An, et al., "First-Principles Study of Methane Dehydrogenation on a Bimetallic Cu/N(111) Surface," The Journal of Chemical Physics, vol. 131, dated 2009, pp. 174702-1-174702-11, (12 pgs.).
Shah, et al., "Supported Binary Catalysts for Dehydrogenation of Methane," Fuel Chemistry Division Preprints, vol. 47, No. 1, dated 2002, pp. 132-133 (2 pgs.).
Eltron Research & Development "Oxidative Dehydrogenation of Methane and Ethane Using Catalytic Membrane Reactors," Technical Brief, dated 2008 (3 pgs.).
Galceran, et al., "Sol-gel Modified Pechini Method for Obtaining Nanocrystalline KRE(WO4)2 (RE = Gd and Yb)," Journal Sol-Gel Science Technology, vol. 42, dated 2007, p. 79-88 (10 pgs.).

* cited by examiner

REACTOR AND CATALYST FOR CONVERTING NATURAL GAS TO ORGANIC COMPOUNDS

CROSS-REFERENCE TO RELATED APPLICATIONS

This application claims the benefit under 35 U.S.C. §119 (e) of U.S. Provisional Patent application No. 61/723,228 filed Nov. 6, 2012, the disclosure of which is hereby incorporated herein by reference.

STATEMENT REGARDING FEDERALLY SPONSORED RESEARCH OR DEVELOPMENT

Not Applicable.

FIELD OF THE INVENTION

The present invention relates generally to converting natural gas to organic compounds. More particularly, the present invention relates to utilizing novel catalysts and reactor designs to convert natural gas to more valuable organic compounds.

BACKGROUND

Natural gas, consisting primarily of methane, is an important fuel source. Natural gas also contains alkanes such as ethane, propane, butanes, and pentanes. Alkanes of increasing carbon number are normally present in decreasing amounts in crude natural gas. Carbon dioxide, nitrogen, and other gases may also be present. Most natural gas is situated in areas that are geographically remote from population and industrial centers. It is often difficult to utilize natural gas as an energy resource because of the costs and hazards associated with compression, transportation, and storage of natural gas.

Various efforts have been made to convert natural gas (primarily methane) to organic carbon compounds, including liquid hydrocarbons and simple alcohols such as methanol. For example, one method is a two-step conversion process. In the first step, methane is reformed with water vapor (also called steam reforming) to produce carbon monoxide and hydrogen (i.e., synthesis gas or "syngas"):

$$CH_4 + H_2O \rightarrow CO + 3H_2$$

In a second step, the produced syngas is converted to hydrocarbons. For instance, Sasol Ltd. of South Africa utilizes the Fischer-Tropsch process and utilizes both natural gas and coal feedstock to provide fuels that boil in the middle distillate range. Middle distillates may be defined as organic compounds that are produced between the kerosene and lubricating oil fractions in the refining processes. Middle distillates include light fuel oils and diesel fuel as well as hydrocarbon waxes.

It is also possible to convert natural gas to syngas via catalytic partial oxidation. In this process, natural gas is mixed with air, oxygen-enriched air, or oxygen, and introduced to a catalyst at elevated temperatures and pressures. The partial oxidation of methane yields a syngas mixture with a $H_2$:CO molar ratio of 2:1, as shown below:

$$CH_4 + \tfrac{1}{2}O_2 \rightarrow CO + 2H_2$$

The partial oxidation reaction is exothermic and requires the catalyst to be in the oxidative state, while the steam reforming reaction is strongly endothermic and requires the catalyst to be in a reduced state. Because the partial oxidation reaction is exothermic, it is difficult to control the reaction temperature in the catalyst bed. This is particularly true when scaling up the reaction from a micro reactor (e.g., ¼ in (about 6 mm) diameter reactor tube and less than 1 gram of catalyst) to a larger scale commercial reactor unit. This is because of the additional heat generated in large reactors relative to the limited heat transfer area available. If heat is not removed such that temperature control may be maintained, partial oxidation may transition to full oxidation, with the major quantity of end products being relatively low value carbon dioxide and water instead of syngas.

Conventional commercial means of converting methane into organic compounds involves first conversion to syngas followed by conversion to organic compounds via Fischer Tropsch process. This is often followed by cracking of the organic longer chain compounds to shorter chain compounds that may be used as a transportation fuel. There have been attempts to combine or eliminate one or more of these steps. U.S. Pat. No. 6,806,087 by Kibby et al. describes the use of two or more types of catalysts used simultaneously or in series for multi-step syntheses where optimum combination may be one that is the optimum for the first step or for the second step. United States Patent Application 2010/0307726 describes a Multi-Stage Multi-Tube Shell-and-Tube Reactor in an attempt to control different reactions within a single reactor. Other known technology utilizes complex reactor design in attempts to control various chemical reactions within a single reactor. United States Patent Application Publication 2003/0194362 by Rogers et al. discloses a multilayered porous ceramic chemical reactor. European Patent Application EP1584603A2 by Christensen et al. discloses a steam reforming reactor comprising a porous ceramic coated with catalyst. There are also various catalyst designs that have been disclosed that include porous designs in pellet and other geometric forms. U.S. Pat. No. 4,863,712 by Twigg, et al. discloses a catalyst comprising nickel and/or cobalt supported on shaped pieces of a silica-free ceramic foam having a network of irregular passages. There is still a need in the industry for a method of converting methane into high molecular weight organic compounds that is scalable with the ability to control temperatures in a less complex reactor design.

It is predicted that natural gas will outlast oil reserves by a significant margin and large quantities of natural gas are available in many areas worldwide. Therefore, there is continuing need and interest in developing methods, systems, and catalysts to convert natural gas to organic compounds in an economical fashion to better utilize this resource.

SUMMARY

Herein disclosed is a reactor comprising a housing; an inlet tube having a section with perforations along its length, wherein the inlet tube section is within the reactor housing; an outlet tube having a section with perforations along its length, wherein the outlet tube section is within the reactor housing; and at least one cylinder made of sintered metal contained within the reactor housing, wherein the sintered metal is catalytically active.

In an embodiment, the sintered metal in the reactor comprises a porous metallic multifunctional (PMM) catalyst comprising (a) a catalyst that promotes the oxidative coupling of methane (OCM) and a methane steam reforming (MSR) catalyst, wherein the catalyst composition causes oxidative dehydrogenation to form reactive species and oligomerization of the reactive species to produce the organic compounds; or (b) a catalyst that promotes syngas generation (SG) and a Fischer-Tropsch (FT) catalyst wherein the catalyst composition causes non-oxidative dehydrogenation to form reactive species and oligomerization of the reactive species to produce the organic compounds; or (c) a SG catalyst, a MSR catalyst, and a FT catalyst wherein the catalyst composition causes non-oxidative dehydrogenation to form reactive species and oligomerization of the reactive species to produce the organic compounds; or (d) a FT catalyst and a MSR catalyst wherein the catalyst composition causes reforming reactions and chain growing reactions to produce the organic compounds.

In an embodiment, the reactor comprises two or more cylinders. In an embodiment, the at least one cylinder is concentric with respect to the reactor housing. In an embodiment, the residence time through the sintered metal is in the range of 0.1 to 5000 microseconds. In an embodiment, the reactor has pressure differential across the sintered metal.

Further disclosed is a reactor system comprising a first reactor and a second reactor as disclosed herein; wherein the first reactor outlet is fluidly connected to the second reactor inlet.

In an embodiment, the reactor system further comprises an inter-reactor gas injector. In an embodiment, the reactor system further comprises inter-reactor heat addition or heat removal.

Also described herein is a method comprising utilizing the reactor as disclosed herein to produce organic compounds from a feed stream comprising methane and steam and optionally hydrogen. In an embodiment, a method comprises utilizing the reactor system as disclosed herein to produce organic compounds from a feed stream comprising methane and steam and optionally hydrogen.

Disclosed herein is a shell and tube reactor comprising a shell and a multiplicity of sintered metal tubes contained within the shell, wherein the sintered metal tubes are catalytically active; an inlet and an outlet for a heat exchange medium; and an inlet for reactants and an outlet for products.

In an embodiment, the sintered metal tubes in the reactor comprise a porous metallic multifunctional (PMM) catalyst comprising (a) a catalyst that promotes the oxidative coupling of methane (OCM) and a methane steam reforming (MSR) catalyst, wherein the catalyst composition causes oxidative dehydrogenation to form reactive species and oligomerization of the reactive species to produce the organic compounds; or (b) a catalyst that promotes syngas generation (SG) and a Fischer-Tropsch (FT) catalyst wherein the catalyst composition causes non-oxidative dehydrogenation to form reactive species and oligomerization of the reactive species to produce the organic compounds; or (c) a SG catalyst, a MSR catalyst, and a FT catalyst wherein the catalyst composition causes non-oxidative dehydrogenation to form reactive species and oligomerization of the reactive species to produce the organic compounds; or (d) a FT catalyst and a MSR catalyst wherein the catalyst composition causes reforming reactions and chain growing reactions to produce the organic compounds.

In an embodiment, the heat exchange medium is a cooling medium. In an embodiment, the cooling medium is oleaginous.

In an embodiment, a reactor system comprises two or more shell and tube reactors configured in series or in parallel.

Also disclosed is a method of performing a reaction comprising providing a shell and tube reactor comprising a shell and a multiplicity of sintered metal tubes contained within the shell; an inlet and an outlet for a heat exchange medium; and an inlet for reactants and an outlet for products; wherein the sintered metal tubes comprise porous catalytic material; and converting the reactants to the products under the action of the catalytic material.

In an embodiment, the pressure of the reactants is higher than the pressure of the heat exchange medium. In an embodiment, the heat exchange medium is inert.

In an embodiment, the reaction comprises the conversion of syngas to methanol, the conversion of methane to methanol, or dimethyl ether. In an embodiment, the reaction is exothermic and the heat exchange medium is a cooling medium. In an embodiment, the cooling medium is oleaginous.

Further disclosed is a reactor comprising an impermeable housing; at least one inlet; at least one outlet; and a catalytically active porous section contained within the housing.

In an embodiment, the catalytically active porous section is made of sintered metal or ceramic or both. In an embodiment, the catalytically active porous section comprises a porous metallic multifunctional (PMM) catalyst comprising (a) a catalyst that promotes the oxidative coupling of methane (OCM) and a methane steam reforming (MSR) catalyst, wherein the catalyst composition causes oxidative dehydrogenation to form reactive species and oligomerization of the reactive species to produce the organic compounds; or (b) a catalyst that promotes syngas generation (SG) and a Fischer-Tropsch (FT) catalyst wherein the catalyst composition causes non-oxidative dehydrogenation to form reactive species and oligomerization of the reactive species to produce the organic compounds; or (c) a SG catalyst, a MSR catalyst, and a FT catalyst wherein the catalyst composition causes non-oxidative dehydrogenation to form reactive species and oligomerization of the reactive species to produce the organic compounds; or (d) a FT catalyst and a MSR catalyst wherein the catalyst composition causes reforming reactions and chain growing reactions to produce the organic compounds.

In an embodiment, the reactor further comprises at least one gas distribution device. In an embodiment, the at least one gas distribution device is inserted at the center of the catalytically active porous section or inserted inside the catalytically active porous section or both. In an embodiment, the at least one gas distribution device is inserted adjacent the catalytically active porous section. In an embodiment, the at least one gas distribution device is fluidly connected with the at least one inlet or at least one outlet or both. In an embodiment, the at least one gas distribution device is a sintered metal tube or a tube with perforations.

In an embodiment, the reactor further comprises a heat exchange device. In an embodiment, the heat exchange device is an integral part of the reactor. In an embodiment, the heat exchange device is a jacket or sleeve that encloses the catalytically active porous section and provides passage for a heat exchange medium. In an embodiment, the heat exchange medium is an inert fluid with respect to the reactions taking place in the reactor. In an embodiment, the heat exchange medium is a reactant with respect to the reactions taking place in the reactor.

In an embodiment, the reactor is utilized to produce organic compounds from a gas stream comprising steam and methane. In an embodiment, the reactor is utilized for hydroformylations, hydrocracking, isodewaxing, isomerizations, dehydrogenations, olefin metathesis, polymerization, paraffin redistribution, alkylbenzene redistribution, or naphtha reforming.

In an embodiment, the residence time through the catalytically active porous section is in the range of 0.1 to 5000 microseconds.

In an embodiment, the reactor has pressure differential across the catalytically active porous section.

The foregoing has outlined rather broadly the features and technical advantages of the invention in order that the detailed description of the invention that follows may be better understood. Additional features and advantages of the invention will be described that form the subject of the claims of the invention. It should be appreciated by those skilled in the art that the conception and the specific embodiments disclosed may be readily utilized as a basis for modifying or designing other structures to accomplish the same purposes of the invention. It should also be realized by those skilled in the art that such equivalent constructions do not depart from the spirit and scope of the invention as set forth in the appended claims.

BRIEF DESCRIPTION OF THE DRAWINGS

For a more detailed description of the preferred embodiments of the present disclosure, reference will now be made to the accompanying drawings, wherein:

FIG. 3b illustrates a cross section of the reactor shown in FIG. 3a.

FIG. 5a is a picture of a sample reactor. FIG. 5b is a schematic illustration of the sample reactor (top) and a cross section view of the sample reactor where the porous or sintered metal is constructed (bottom).

NOTATION AND NOMENCLATURE

Figure 1A:
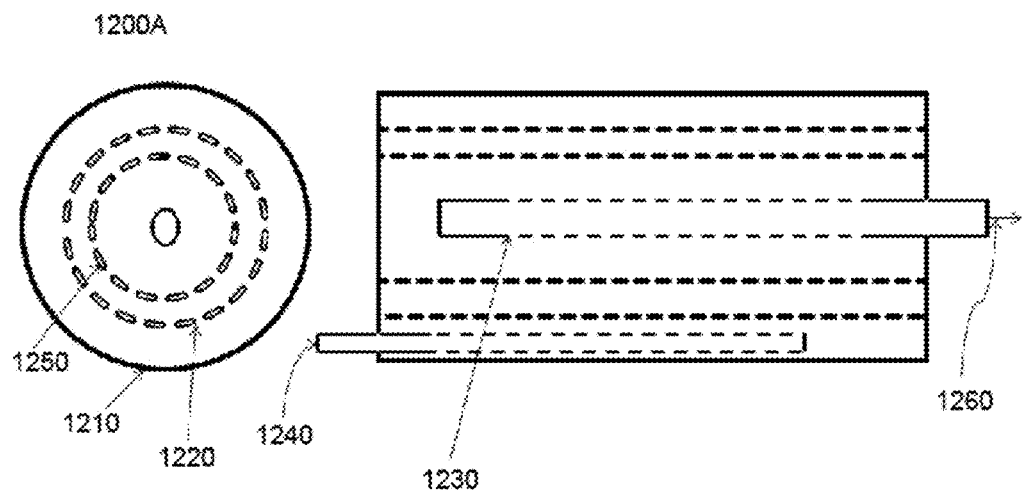
FIG. 1a illustrates a multi layer sintered metal reactor in accordance with certain embodiments of this disclosure.

For nomenclature purposes, reference to Groups from the Periodic Table of the Elements refers to the IUPAC Periodic Table of Elements (Jun. 22, 2007 version) published by the International Union of Pure and Applied Chemistry (IUPAC).

In this disclosure, a syngas generating catalyst, which is abbreviated as SG catalyst for ease of reference. A Fischer-Tropsch catalyst is abbreviated as FT catalyst for ease of reference. A methane steam reforming catalyst is abbreviated as MSR catalyst for ease of reference, which is equivalent to a steam methane reforming catalyst or a steam reforming catalyst. A catalyst that promotes oxidative coupling of methane is abbreviated as OCM catalyst for ease of reference. In this disclosure, the use of the terms SG, FT, MSR, and/or OCM catalysts serves the purpose of referring to these categories of catalysts but does not limit these catalysts in their function according to the conventional understanding of the art. The reactions that these catalysts promote or activate should be understood in the context of this disclosure.

As used herein, the term 'sintered metal' refers to powdered metal that is compressed and sintered. 'Sintered metal' also refers to powdered metal that is compressed and sintered and then coated with a catalyst by means known to one skilled in the art such that the sintered metal possesses a catalytic surface. 'Sintered metal' also refers to powdered metal that is coated with catalyst by means known to one skilled in the art and then compressed and sintered. The specific meaning of this term will be clear in the context of its use.

In this disclosure, the various reactor designs are called "porous metal reactor" in totality.

In this disclosure, oxidative coupling of methane (OCM) includes both complete oxidation and partial oxidation of methane. In most cases, partial oxidation of methane occurs unless otherwise specified. During partial oxidation of methane, intermediate species, such as $CH_3$, $CH_2$, and $CH$, are generated, which participate in the formation of organic compounds.

In this disclosure, percentages for gases are volume based and percentages for solids are weight based unless otherwise specified.

Certain terms are used throughout the following description and claims to refer to particular system components. This document does not intend to distinguish between components that differ in name but not function.

In the following description and in the claims, the terms "including" and "comprising" are used in an open-ended fashion, and thus should be interpreted to mean "including, but not limited to . . . ".

DETAILED DESCRIPTION

Overview. In an embodiment, a method of producing organic compounds comprises contacting a reactant gas mixture, comprising natural gas and steam with a Porous Metallic Multifunctional (PMM) Catalyst. In some embodiments, the feed includes hydrogen. In some embodiments, the feed also includes carbon oxides and hydrogen.

In some embodiments, the PMM catalyst comprises a MSR catalyst and a FT catalyst. In some embodiments, the PMM catalyst comprises a SG catalyst, a MSR catalyst, and a FT catalyst. In some embodiments, the PMM catalyst comprises a SG catalyst and a FT catalyst. In some embodiments, the PMM catalyst comprises an OCM catalyst and a MSR catalyst.

In this disclosure, the formation of organic compounds is initiated by the removal of one or more hydrogen's (H) from methane ($CH_4$), thereby creating reactive species (e.g., $CH_3$, $CH_2$, and/or $CH$). The reactive species then combine to form organic compounds (e.g., methanol, C2+compounds). In some cases, dehydrogenation (hydrogen removal) from methane involves the use of oxygen, which is termed oxidative dehydrogenation herein. In some cases, dehydrogenation (hydrogen removal) from methane does not involve the use of oxygen, which is termed non-oxidative dehydrogenation herein. For example, oxidative dehydrogenation reactions may utilize metal catalysts such as OCM catalysts; and non-oxidative dehydrogenation reactions may utilize metals in MSR catalysts.

Herein various catalytic reactions are cited such as OCM, FT, MSR, and SG. Various metals, metal combinations and metal states (i.e. oxides) are noted to promote these reactions. In certain cases, a metal is used under different conditions and/or in different states to promote different reactions. For example, nickel in its oxidized state is used as a promoter of oxidation of hydrocarbons; nickel in its reduced state is used as a hydrogenation catalyst in the presence of hydrogen and unsaturated hydrocarbons. Reduced nickel is also used in methane steam reforming ($CH_4+H_2O \rightarrow CO+3H_2$).

Furthermore, a PMM catalyst as disclosed herein is able to promote multiple reactions in a single reactor configuration.

MSR Catalysts. In an embodiment, the MSR catalyst of this disclosure comprises a metal selected from the group consisting of cobalt (Co), iron (Fe), molybdenum (Mo), tungsten (W), cerium (Ce), rhodium (Rh), platinum (Pt), palladium (Pd), titanium (Ti), zinc (Zn), nickel (Ni), ruthenium (Ru), and combinations thereof. In an embodiment, the MSR catalyst comprises rhodium (Rh) catalysts, nickel (Ni) catalysts, ruthenium (Ru) catalysts, platinum (Pt) catalysts, or palladium (Pd) catalysts. Examples of rhodium catalysts include rhodium coated $\alpha$-$Al_2O_3$ foam monoliths and Ce—$ZrO_2$-supported Rh catalyst. Examples of nickel catalysts include unsupported nickel powder catalysts, ceramic-supported nickel catalysts, Ce—$ZrO_2$-supported Ni catalysts, doped ceria supported Ni—Cu catalyst, and $\alpha$-$Al_2O_3$-supported nickel catalyst. Examples of ruthenium catalysts include Ru-added to Ni catalysts supported on $Al_2O_3$, $La_2O_3$, MgO, or $MgAl_2O_4$, and bimetallic catalysts comprising Ru and Ni. Examples of platinum catalysts include Pt/$Al_2O_3$, Pt/$ZrO_2$ and Pt/$CeO_2$ catalysts prepared, for example, by incipient wetness impregnation of calcined $\gamma$-alumina (Engelhard Corporation Catalyst), zirconium hydroxide (MEL Chemicals), and cerium ammonium nitrate (Aldrich) supports. Examples of palladium catalysts include alumina supported palladium catalysts and Pd/ZnO catalysts prepared by impregnation or micro-emulsion techniques. Other MSR catalysts include those disclosed in U.S. Pat. Nos. 7,670,987, 7,687,051, 7,687,050, 7,470,648, 7,569,511, and 6,355,589, the disclosures of which are hereby incorporated herein by reference for all purposes. A general treatment after the synthesis of a reforming catalyst is calcination (heating the sample in air, in order to clean up and stabilize the catalyst) and/or reduction of the catalyst (heating the sample in a reducing atmosphere containing hydrogen, in order to activate the catalytic metal). It is within the scope of this disclosure to utilize a MSR catalyst as known to one skilled in the art to form a PMM catalyst as described herein.

SG Catalysts. In an embodiment, the SG catalyst of this disclosure includes various oxides, halides and carbonates of both alkali and alkaline earth metals, transition metals, and combinations thereof. In an embodiment, a SG catalyst produces syngas from methane and carbon dioxide.

In an embodiment, the SG catalysts of this disclosure refer to those catalysts that produce/generate syngas other than MSR catalysts, for example, a metal-based catalyst that generates syngas from a carbon source (e.g., biomass). Such a SG catalyst contains a transition metal or noble metal, in combination with a lanthanide. In some cases, the lanthanide is cerium or lanthanum. In some cases, such a SG catalyst comprises Ni, Pd, Pt, Co, Rh, Ir, Fe, Ru, Os, Cu, Ag, Au, Re, or a combination thereof. In some cases, the metal-based SG catalyst is a rhodium-cerium catalyst. Further details of such SG catalysts are in US Patent Application Publication Nos. 20100200810 and 20110047864. It is within the scope of this disclosure to utilize a SG catalyst as known to one skilled in the art to form a PMM catalyst as described herein.

FT Catalysts. In embodiments, Fischer-Tropsch (FT) catalyst of this disclosure includes a Group VIII transition metal. Such transition metals include cobalt, iron, and ruthenium. In an embodiment, the FT catalyst comprises cobalt as the active component to promote the conversion reactions. In some cases, the FT catalyst also contains one or more noble metal promoters. The FT catalyst is able to produce organic compounds (e.g., $C_2H_6$, $C_nH_{2n+2}$, n=2,3,4, ... or higher numbers, or $C_nH_{2n}$, n=2,3,4 ...) from syngas. A variety of catalysts may be used for the FT process, but the most common are the transition metals cobalt, iron, and ruthenium. In some cases, Nickel is used, but tends to favor methane formation ("methanation"). In an embodiment, the FT catalyst of this disclosure includes those for iso-synthesis, e.g. formation of iso-paraffins, and iso-olefins, such as (1) ZnO—$Al_2O_3$, (2) $Al_2O_3$, (3) $ThO_2$, (4) ZnO with $ThO_2$ or $ZrO_2$, (5) $ThO_2$—$Al_2O_3$. It is within the scope of this disclosure to utilize a FT catalyst as known to one skilled in the art to form a PMM catalyst as described herein.

OCM Catalysts. In an embodiment, the OCM catalyst comprises a transition metal. In an embodiment, the OCM catalyst comprises an alkali metal. In an embodiment, the alkali metal is selected from the group consisting of lithium, sodium, potassium, rubidium, cesium, and mixtures thereof.

In an embodiment, the OCM catalyst comprises a pervoskite structure. In an embodiment, the OCM catalyst comprises a promoter. In an embodiment, the promoter is in a crystal state.

In an embodiment, the OCM catalyst comprises a Group 2 metal. In an embodiment, the metal is selected from the group consisting of strontium, calcium, barium, and magnesium.

In an embodiment, the OCM catalyst comprises a component selected from the group consisting of sodium oxide, cobalt oxide, tungsten oxide, silicon oxide, manganese oxide, and combinations thereof. In an embodiment, the OCM catalyst comprises silicon nitride. In an embodiment, the OCM catalyst is a supported catalyst. In various embodiments, the support is an inert material having high surface area. In various embodiments, the OCM catalyst comprises a promoter.

In an embodiment, the OCM catalyst is a nickel-based catalyst. In an embodiment, the OCM catalyst is a cobalt-based catalyst. In an embodiment, the OCM catalyst comprises magnesium, manganese, or combination thereof. In an embodiment, the OCM catalyst comprises oxides of magnesium, oxides of manganese, or combinations thereof.

In an embodiment, the OCM catalyst comprises an alkali metal oxide. In an embodiment, the OCM catalyst comprises a rare earth metal oxide.

Other examples of the OCM catalyst and preparation methods may be found in U.S. Pat. Nos. 7,291,321; 7,250,543; 6,096,934; 5,877,387; 5,849,973; 5,736,107; 5,599,510; 5,321,185; 5,132,482; 5,132,481; 5,118,654; 5,097,086; 5,066,629; 4,956,327; 4,945,078; 4,935,572; and 4,826,796, the disclosures of which are hereby incorporated herein by reference for all purposes. It is within the scope of this disclosure to utilize an OCM catalyst as known to one skilled in the art to form a PMM catalyst as described herein.

Other PMM Catalysts. In a further embodiment, a PMM catalyst comprises oxide(s) of Zn, oxide(s) of Mn, oxide(s) of Co, oxide(s) of Ni, oxide(s) of Mg, or oxide(s) of Fe. When this catalyst is contacted with steam and methane, the overall reaction is:

$13CH_4+14H_2O \rightarrow 2C_2H_4+4CO+5CO_2+36H_2$.

In an embodiment, steam and methane are reacted under the action of such PMM catalyst at a temperature of about 900° C.

Formation of PMM Catalyst. In an embodiment the PMM catalysts of this disclosure are fabricated utilizing combinations of powdered metal oxides and/or metal salts that promote two or more of reactions encompassing SG, MSR, FT, and OCM reactions. Selection of the type metal to promote each reaction is determined by the reactivity and selectivity of the metal to produce the desired reaction product but also by the ability of the metal to withstand the operating conditions required to produce the desired reaction products without melting or sintering.

In an embodiment, a PMM catalyst is formed by dry blending a powder MSR catalyst and a powder FT catalyst. In an embodiment, a PMM catalyst is formed by dry blending a powder MSR catalyst, a powder SG catalyst, and a powder FT catalyst. In an embodiment, a PMM catalyst is formed by dry blending a powder SG catalyst and a powder FT catalyst. In an embodiment, a PMM catalyst is formed by dry blending a powder MSR catalyst and a powder OCM catalyst.

In some embodiments, the PMM catalyst is formed into a sintered powder or deposited on an inert support. The inert support may comprise, without limitation, alumina, zeolite, zirconia, silica, glass, magnesia, a metal, or a metal oxide. Other types of inert support are known in the art and within the scope of this disclosure. In some cases, the inert support comprises a high surface area substrate. In some cases, the inert support comprises a porous substrate. The use of high surface area substrate in a support increases catalytic activity. In some cases, the use of high surface area substrate enables the use of reduced metal content.

In some embodiments, the PMM catalyst is further treated. For example, the MSR reaction requires the reforming metal in the catalyst to be reduced (metal and not oxides). Reduction of the steam reforming component of the PMM catalyst may be by means of hydrogen at temperatures in excess of 180° C. The catalyst is reduced by passing a carrier gas such as nitrogen, natural gas, or steam through the catalyst and adding controlled amounts of hydrogen. For example, the catalyst is reduced in situ by heating to 180° C. for 4 h followed by 12 h at 230° C. in a gas mixture of 1% hydrogen/99% nitrogen (vol % or mol %). The activated catalyst is, however, pyrophoric. Upon exposure to air, the catalyst must be re-reduced and stabilized by surface oxidation. For steam-reforming, Ni or the noble metals Ru, Rh, Pd, Ir, Pt are used as the active metal in catalysts. Because of its low costs, Ni is the most widely used metal from this set. Ni, however, is less active than other of these metals. These metals may be incorporated as powdered porous metal shape or deposited on supports that are fabricated into a porous shape as defined herein. Among the most common supports for methane reforming are alpha- and gama-$Al_2O_3$, MgO, $MgAl_2O_4$, $SiO_2$, $ZrO_2$, and $TiO_2$. In the case of methane reforming, promoters to inhibit carbon deposition on the active metal may be added. Suppression of carbon formation on (Ni-based) catalysts is achieved by adding small amounts of an alkali metal to the catalyst.

In another embodiment, a PMM catalyst comprising an OCM catalyst is prepared by a process comprising crushing the OCM catalyst; mixing the crushed OCM catalyst with a MSR catalyst to form a catalyst mixture; pelletizing the catalyst mixture to form catalyst pellets; crushing the catalyst pellets and annealing the crushed catalyst pellets at increasing temperatures with a predetermined temperature-time profile. In some cases, preparing the OCM catalyst comprises forming an aqueous slurry comprising an alkaline earth metal salt, a powdered metal salt, and a powdered transition metal oxide; adding a polymeric binder to the slurry to form a paste; drying the paste to form a powder; heating the powder at increasing temperatures at a predetermined temperature-time profile commensurate with the polymeric binder; and calcining the heated powder to form the OCM catalyst.

In an embodiment, the PMM catalyst comprises a dry blend of an OCM catalyst and an MSR catalyst. In an embodiment, an OCM catalyst and an MSR catalyst are deposited on a support to form a PMM catalyst. Under conventional operating conditions the Oxidative Coupling reaction requires the OCM component of the PMM catalyst to be activated and the metals in the OCM catalyst component exist in an oxide form.

Herein the PMM catalyst is utilized in the reduced state to produce mainly syngas with some minor amounts of organic compounds produced. The methane steam reforming reaction requires the reforming metal in the PMM catalyst to be reduced (metal and not oxides). Reduction of the steam reforming component of the PMM catalyst may be by means of hydrogen at temperatures in excess of 180° C. For steam-reforming, Ni or the noble metals Ru, Rh, Pd, Ir, Pt are used as the active metal in catalysts. Because of its low costs, Ni is the most widely used metal from this set. Ni, however, is less active than the other metals. These metals may be on supports, which are among the most common for methane reforming such as alpha- and gama-$Al_2O_3$, MgO, $MgAl_2O_4$, $SiO_2$, $ZrO_2$, and $TiO_2$. In the case of methane reforming, promoters to inhibit carbon deposition on the active metal may be added. Suppression of carbon formation on (Ni-based) catalysts is achieved by adding small amounts of an alkali metal to the catalyst.

In an embodiment, the content of OCM catalyst in the PMM catalyst is in the range of from 91 wt % to 99 wt %, alternatively from 71 wt % to 89 wt %, alternatively from 50 wt % to 70 wt %, with the balance of the catalyst being a MSR catalyst. In an embodiment, the ratio between an OCM catalyst and a MSR catalyst in a PMM catalyst is 99:1; alternatively 90:10; alternatively 80:20; or alternatively 70:30. In an embodiment, the weight ratio between an OCM catalyst and an MSR catalyst is in the range of from about 50:1 to about 99:1. In embodiments, silicon nitride is incorporated with an MSR catalyst if increasing the fusion temperature of the catalyst is desired.

In an embodiment, a PMM catalyst comprises an OCM catalyst, wherein the OCM catalyst comprises a transition metal oxide, an alkali metal oxide, and an alkaline earth metal oxide; a MSR catalyst; a semimetal oxide; and a semimetal nitride. In some cases, the transition metal comprises cobalt or tungsten, the alkali metal comprises sodium, the alkaline earth metal comprises manganese, and the semimetal comprises silicon.

Without being limited by theory, the combination of metals or metal oxides in PMM catalysts may also promote reduction of carbon dioxide, if present, in the presence of hydrogen. It is known that the presence of oxides of Group 3 and Group 4 elements in combination with transition metals of Groups 8, 9, and 10 may promote reduction of carbon dioxide in the presence of hydrogen. Further examples of such catalysts are listed in U.S. patent application Publication No. 20070149392 and U.S. Pat. Nos. 5,911,964 and 5,855,815, the disclosures of which are hereby incorporated herein by reference in their entirety for all purposes.

In an embodiment, a PMM catalyst composition for producing syngas and minor amounts of organic carbon compounds when operated in a reducing atmosphere (e.g., absent of oxygen and present of hydrogen) comprises 0.1-99 wt % of rhodium. In some cases, the catalyst composition comprises 10-90 wt % of rhodium. In some cases, the catalyst composition comprises 20-80 wt % of rhodium. In some cases, the catalyst composition comprises 30-70 wt % of rhodium. In some cases, the catalyst composition comprises 40-60 wt % of rhodium. In some cases, the catalyst composition comprises more than 50 wt % of rhodium.

In some embodiments, addition of halogen by adding, for example, chlorine or a chlorine-containing compound further enhances catalyst life and selectivity to hydrocarbons. In some cases, halogen or a halogen-containing compound is added to the mixture to give a final concentration ranging from about 0.001% volume/volume ("v/v") to about 0.04% v/v. In other cases, halogen or a halogen-containing compound is added to a final concentration ranging from about 0.008% v/v to about 0.02% v/v. Halogen may be introduced in any form to the catalyst composition.

Use of PMM Catalyst. In embodiments, the reaction temperature for utilizing the PMM catalyst is in the range of from about 300° C. to about 1000° C.; alternatively from about 300° C. to about 900° C.; alternatively from about 350° C. to about 950° C. In embodiments, the reaction temperature for utilizing the PMM catalyst is in the range of from about 400° C. to about 875° C.; or alternatively from about 400° C. to about 850° C.; or alternatively from about 450° C. to about 850° C. In some cases, the reaction temperature is in the range of from about 700° C. to about 900° C.; alternatively from about 750° C. to about 875° C.; or alternatively from about 775° C. to about 850° C.

In embodiments, the reaction pressure is in the range of from about 20 kPa to about 25,000 kPa; or alternatively from about 50 kPa to about 10,000 kPa; or alternatively from about 70 kPa to about 10,000 kPa. In an embodiment, the reaction pressure is in the range of from about 20 kPa to about 300 kPa.

In an embodiment wherein alcohols are produced, the reaction temperature is in the range of from about 300° C. to about 1200° C. In an embodiment, the reaction pressure is in the range of from about 0.1 atm to about 100 atm.

In an embodiment, the production of organic compounds comprises contacting a reactant gas mixture comprising natural gas and steam with optional addition of hydrogen and carbon oxides with a PMM catalyst as described herein. In embodiments, the reactant gas may first be treated by means known to those skilled in the art to remove catalyst poisoning compounds such as sulfur-containing compounds.

In an embodiment, a method for producing an organic compound comprises contacting a reactant gas mixture comprising natural gas and steam with optional addition of hydrogen and carbon oxides with a catalytically effective amount of a PMM catalyst. The reactant gas mixture may include other hydrocarbons such as, but not limited to, ethane, propane, butane, hexane, heptane, normal-octane, iso-octane, naphthas, liquefied petroleum gas, and middle distillate hydrocarbons. In some embodiment, the feed gas comprises at least about 50% methane by volume. In some embodiment, the feed gas comprises at least about 80% methane by volume. In certain embodiments, the feedstock is pre-heated before contacting the catalyst.

Operations. The reactors as described herein may be arranged in series or in parallel to achieve desired yield and/or production throughput. In some embodiments, reactors of different designs are used in combination.

Under normal operation conditions, the feed gas consists primarily of methane and steam. In some cases, the methane composition ranges from 5% to 95% (mol %). In some cases, steam ranges from 1% to 95% (mol %).

In some embodiments, molecular oxygen is added to the feed gas when the PMM catalyst becomes fouled. For example, $O_2$ acts in combination with the OCM catalyst to de-coke and regenerate the catalyst. In some embodiments, the feed gases are cycled between oxidative and reducing atmospheres. In an embodiment, the methane:oxygen:steam molar ratio ranges from about 1:1:1 to about 4:1:1. In an embodiment, the methane:oxygen:steam molar ratio ranges from about 1:1:1 to about 1:1:4. In an embodiment, the methane:oxygen:steam molar ratio ranges from about 10:1:10 to 1:1:10. In an embodiment, the methane:oxygen:steam molar ratio ranges from about 10:1:10 to 1:4:1.

In certain embodiments, the molar ratio of steam to natural gas in the feed is in the range of from about 1:1 to about 3:1; alternatively from about 5:1 to about 10:1; alternatively from about 10:1 to about 50:1; alternatively from about 200:1 to about 1:1.

In certain embodiments, the reactant gas mixture is passed over the catalyst at a space velocity of from about 200 to about 30,000 normal liters of gas per hour per liter of catalyst per hour (NL/L/h), alternatively from about 500 to 10,000 NL/L/h.

Figure 1B:
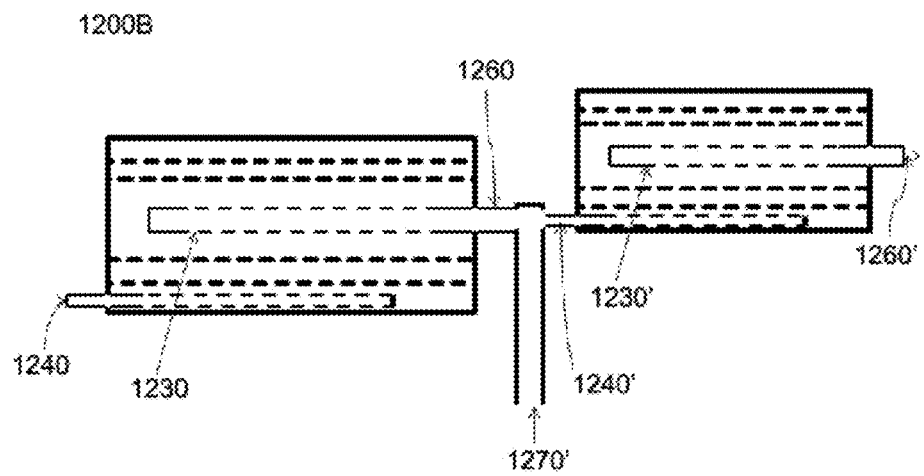
FIG. 1b illustrates a stacked multi layer sintered metal reactor in accordance with certain embodiments of this disclosure.

Multi Layer Sintered Metal Reactor. In an embodiment, a PMM catalyst as described herein is pressed into a cylinder (or any other suitable shape as deemed appropriate by one skilled in the art) and placed in a reactor 1200 as shown in FIG. 1*a* and FIG. 1*b*.

The fusing of the PMM metal catalyst may be by conventional sintered metal techniques or enhanced by known fluxing agents. Alternatively, the porous substrate may be formed using ceramics (i.e. alumina-silicate, Zeolite; $SiO_2$; $Al_2O_3$) and then the PMM catalyst is coated on the surface of the porous ceramic substrate. Herein 'porous substrate' refers to a catalytically active article formed by compacting a mixture of powdered metal oxides and/or alumina silicate ceramic, either individually or in combination into a suitable shape and size to be incorporated into a reactor. Several techniques for producing and controlling pore size in the porous substrate are known to those skilled in the art. U.S. Pat. No. 4,073,999 by Bryan et al. describes a porous ceramic structure prepared by placing calcium carbonate in the ceramic. Upon heating, the calcium carbonate decomposes into calcium oxide and carbon dioxide creating porosity in the structure. U.S. Pat. No. 5,227,342 by Anderson et al. describes a process for creating metal oxide ceramic materials that permits the control of the porosity in the resulting ceramic material. Coating of PMM catalyst may be by conventional techniques involving solubilizing the metal (either by using a soluble form of metal or dissolving metal compound in a solvent) followed by coating or precipitation of the metal and calcining the coated metal or ceramic to produce an active metallic surface.

In some embodiments, the catalyst metal is deposited by a method called the Pechini that is a sol-gel method (ref: J Sol-Gel Sci Techn (2007) 42:79-88 DOI 10.1007/s10971-006-1517-3) that produces nano-crystals. U.S. Pat. No. 4,409,131 by Fetchin is incorporated herein in its entirety, which describes a process for impregnating a porous alumina or alumina silica substrate with soluble forms of cobalt, nickel and molybdenum. U.S. Pat. No. 4,263,173 by Carter et al. describes the preparation of a nickel-cobalt-silica catalyst which additionally contains co-precipitated copper.

Other examples of nickel catalysts and their use in reforming and other processes include U.S. Pat. Nos. 2,750,261; 3,205,182; 3,351,566; 3,417,029; 3,697,445; 3,859,370; 3,868,332; 4,088,603; and Belgium Pat. No. 841,812. In many of these patents, the catalysts are prepared by co-precipitation or impregnation processes wherein the catalytic metal precursors are either precipitated from solution in the presence of a support material or solution containing said precursor is impregnated into the pores of a porous support material. In British Patent No. 1,220,105, for example, aqueous solutions are employed in conjunction with a homogeneous precipitation procedure to give highly dispersed nickel catalyst. In various embodiments, coating or precipitation of metals on the porous substrate is accomplished by multiple coating and/or precipitation cycles.

In a further embodiment, a PMM catalyst is calcined. Calcining may be in an oxidizing atmosphere to remove organic components followed by reducing the metal compound as described herein to produce a metallic surface. Either sintered metal or metal coated ceramic is formed to produce uniform pore sizes for gases to pass through and to maximize surface area. In an embodiment, the effective orifice size is also a factor of the desired pressure drop across the PMM. In an embodiment, the pressure drop affects the temperature reduction across the PMM. In certain embodiments, the pore size is as small as possible while allowing for residence time of reactant gases over the catalytic surface without carbonizing or excessive heat buildup. In some embodiments, the pore size is from 1 micron to 500 microns. In some embodiments, the pore size is from 1 micron to 100 microns. In some embodiments, the pore size is from 5 microns to 40 microns. In some embodiments, the pore size is from 5 micron to 20 microns. The pore size is related to the porosity of the sintered material and therefore may be more easily controlled.

It is desirable to maintain a high surface area of the PMM catalyst. In some embodiments, the surface area is greater than about 0.1 $m^2/gm$ for sintered metal. In some embodiments, the surface area is greater than about 10 $m^2/gm$ for ceramic substrates. In some embodiments, the surface area is 300-600 $m^2/gm$ for γ-alumina.

Referring to FIG. 1a, reactor 1200A includes two concentric sintered metal cylinders. The sintered metal catalyst cylinders are shown as 1220 and 1250 in FIG. 1a. The feed gases are methane, steam and hydrogen with optional addition of carbon oxides. Syngas (CO and H2) is produced from methane and then converted to hydrocarbons as it passes through the PMM catalytic surfaces.

In an embodiment, the sintered metal catalyst is formed by pressing and sintering powdered cobalt, nickel and rhodium into a formed cylinder (such as 950 as shown in FIG. 3). Various promoters may also be incorporated, including but not limited to Cr, La, Pd, Pt and Cs. The thickness of the sintered metal is such that a residence time over/through the catalytic zone is in the range of 0.1 to 5000 microseconds. In embodiments, the residence time pressure and temperature over the PMM catalyst as well as pore size is controlled so as to maximize conversion of methane and yields to organic compounds without carbon deposition.

In various embodiments, catalytic zone thickness (or sintered material thickness), residence time over/through the catalytic zone, pore size, temperature, and pressure are interrelated factors. The residence time is in the range of 0.1 to 5000 microseconds. In various embodiments, the thickness, pore size, temperature, and pressure are adjusted to ensure the proper residence time. This applies to the various reactor designs as disclosed herein.

In an embodiment, as illustrate by FIG. 1a, reactor 1200A has an inlet tube 1240 that has perforations along its length that is within the reactor 1200A to distribute feed gases evenly across the length of the reactor. The outlet 1260 of the reactor 1200A is also perforated along its length within the reactor to extract effluent gases. Within the reactor 1200A are cylinders made of sintered metal 1220, 1250. The sintered metals are catalytically active. Although two sintered metal cylinders are shown, additional sintered metal cylinders may be utilized. The thickness of the sintered metal cylinders 1220, 1250 varies and is determined by the desired residence time for the feed gases to be exposed to the catalytic metals. In other aspects of the invention the catalytic sintered metal cylinders may be fabricated from porous ceramic compounds such as alumina silicates or zeolites or porous ceramic compounds coated with catalytically active materials.

Reaction gases such as methane, steam, carbon oxides and hydrogen enter through the reactor inlet 1240 and are distributed through an initial catalytic sintered metal cylinder 1220 (may also be catalytic porous ceramic). Catalyst that might be used for the initial catalytic sintered metal cylinder 1220 included those that promote reforming, dehydrogenation, syngas, water-gas-shift and oxidative coupling reactions. The exposure of the feed gases to the initial sintered metal catalytic cylinder 1220 converts a portion of the material to an intermediate compound. Such intermediate compounds include alkenes such as ethylene, propylene, aldehydes, alcohols and other organic compounds and compounds such as hydrogen, oxygen, and ethane.

The reacted and unreacted gases then pass to a second catalytically active sintered metal cylinder 1250 that further converts a portion of the gases to desired compounds such as alcohols, esters, aldehydes, ketones and other compounds.

In an embodiment, additional gases are added between the catalytic sintered metal and/or porous ceramic cylinders. In another embodiment, additional pacifying (heat removal or addition) as well as pressure changes may be incorporated between the sintered metal cylinders.

In FIG. 1a, 1210 is the outer shell of the reactor, which is sealed top and bottom except for inlet 1240 and outlet 1230 tubes. 1230 is a perforated outlet tube located at the center of the reactor for extraction of reacted gases after they pass through the sintered metal/ceramic catalyst (1250 and 1220).

In another embodiment, as illustrated by FIG. 1b, the reactors may be combined in series 1200B. In this configuration exit gas 1260 from the first reactor enters a second reactor inlet 1240' for further reactions. The second reactor in series comprises at least one outlet 1260'. 1230' in the second reactor in series in FIG. 1b is the same as 1230 in FIG. 1a.

Additional inter-stage feed gas 1270' may be added as needed. Inter-stage gases 1270' include steam, methane, carbon oxides or inert gases. Inter-stage gases may also be used to either increase or decrease temperatures or pressures entering downstream reactors.

Temperatures and pressures for operating the reactor(s) are determined by the desired chemical reaction(s) and catalyst activity as known to one skilled in the art. Pressure drop across the catalytically active porous cylinders 1250 and 1220 will depend on the pore size, surface area of the cylinders 1250, 1220, gas flow rate and temperature. Pressure drop is optimized in order to increase turbulence of gases and/or modify the temperature drop across the catalytically active porous cylinders and minimize mass transfer limitations that will impact catalytic activities as well as quench conditions.

The feedstock gases are passed over the catalyst, using any of a variety of space velocities. Space velocities for the process, stated as gas hourly space velocity ("GHSV") may range from about 100 to about 30,000 volumes per hour of feed per volume of catalyst. In embodiments, the GHSV range may be from about 200 to about 15,000 NL/L/h. In an embodiment, the gas flow ranged from about 250 to about 5,000 NL/L/h. The effluent stream of product gases emerges from the reactor. Units of gas flow were measured as normal liters of gas per hour per liter of catalyst (NL/L/h). Since the catalyst is used in sintered metal form, the GHSV may be adjusted based on the actual catalyst content in the reactor. High surface area contained in such reactors may enable the use of less catalyst or higher throughput/GHSV.

$$GHSV = r_{feed}/V$$

$$V = \pi(R_O)^2 H - \pi(R_I)^2 H$$

wherein GHSV=gas hourly space velocity (standard cubic feet per hour/cubic feet)
$r_{feed}$=volume of feed as gas at standard conditions per hour
V=volume of catalyst
H=height of cylinder
$R_O$=outer radius of cylinder
$R_I$=inner radius of cylinder In an embodiment, the catalytically active porous cylinders are externally reinforced if the pressure and/or temperature cause its structural integrity to be compromised.

Shell and Tube Reactor. In an embodiment, a shell and tube reactor is suitable for the conversion of syngas to organic compounds (including alcohols) by means of a sintered metal tube inside a shell and tube heat exchanger.

Figure 2A:
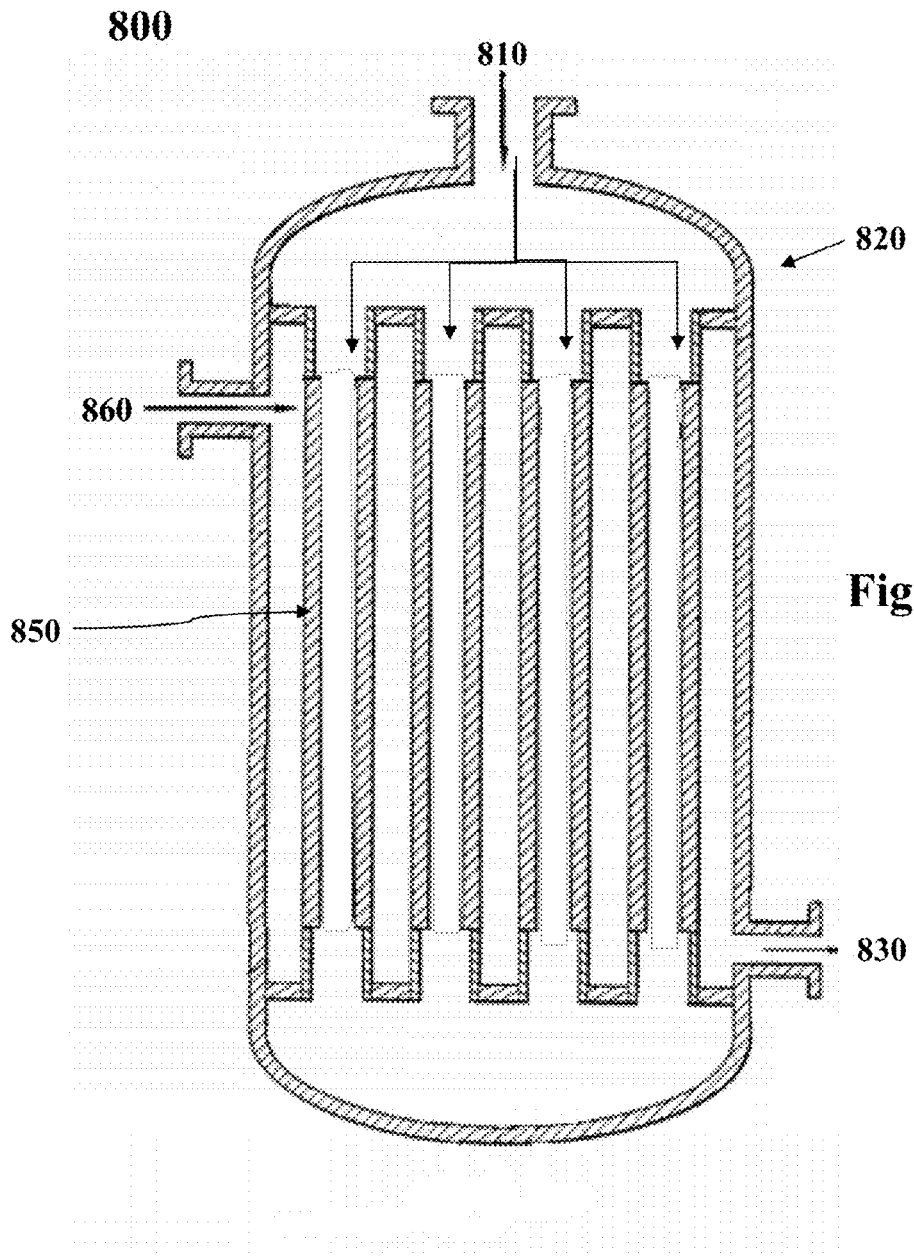
FIGS. 2a-2c illustrate a shell and tube reactor suitable for use with the methods and systems described in accordance with embodiments of this disclosure.
Figure 2B:
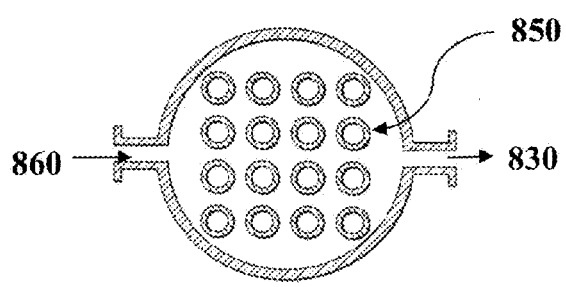
Figure 2C:
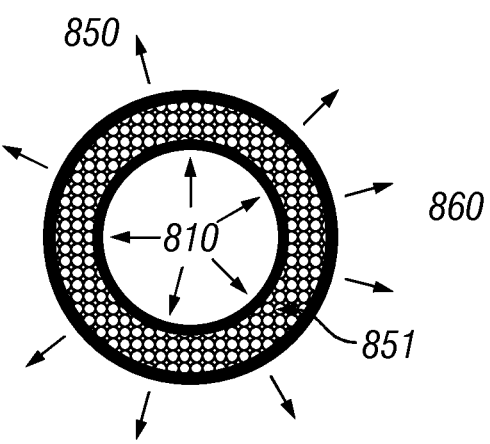

Referring to FIG. 2a, 800 broadly illustrates a shell and tube type reactor. FIG. 2b is a cross section of reactor 800. FIG. 2c is a cross section of a tube inside reactor 800.

In an embodiment, reaction is carried out in a multiple tube reactor 800, having one or more porous catalytic media 851 (as shown in FIG. 2c) formed in the shape of a tube 850 housed in an outer shell 820.

A reactor inlet 860 provides an inert cooling medium (e.g., oil) that surrounds the exterior of the porous catalytic tubes 850. Reactant gases 810 enter the reactor and undergo reaction(s) within the porous catalytic tubes 850. Reacted gases exit the porous catalytic media 851 and are immediately cooled by the cooling medium 860. The reacted gases and cooling oil exit the reactor through an exit port 830 for further processing downstream to remove the reacted gases from the inert cooling medium by means known to one skilled in the art. The cooling material and any unreacted gases may then be recycled.

The pressure of the feed gases 810 is such that it is greater than the pressure of the cooling medium 860 in order to prevent flow of the cooling medium through the porous catalytic material 851 and maintain gas flow through the porous catalytic media and into the inert cooling medium.

Reactor 800 is suitable for reactions requiring rapid cooling such as exothermic reactions and the catalytic material may be any catalyst that promotes exothermic reactions. Feed gas 810 temperatures and pressures are such to promote the desired exothermic reaction when exposed to the porous catalytic material 851. The residence time required for the desired reaction is a factor of flow rates and contact time across the porous catalytic media 851. This contact time may be adjusted for a given flow rate by varying the thickness of the porous catalytic media 851. The benefit of this reactor design is the removal of reaction heat efficiently and economically.

Catalytic reactions include: conversion of syngas to methanol, $CO+2H_2 \rightarrow CH_3OH$ [$\Delta H(298\ k)=-90.6$ kJ/mol], with catalysts (e.g., $CuO-ZnO-Al_2O_3$ and $Cr_2O_3$) at temperatures of 200° C.-300° C. and pressure of 10-100 atm (1-10 MPa). This reaction is exothermic and favored at low temperature. Syngas may be produced from methane or coal. In the case of coal, the syngas may need to be supplemented with additional hydrogen for material balance. In the case of coal, the feed gas contains powdered coal.

Partial oxidation of methane to methanol is another exothermic and catalytic reaction that is suitable for this reactor design as depicted by the reaction below.

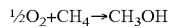

$$\tfrac{1}{2}O_2 + CH_4 \rightarrow CH_3OH$$

This reaction is exothermic with reaction heat of 126 kJ/mol. It may be catalyzed by transition metal oxides, such as, iron copper zeolite (Fe—Cu—ZSM-5); silica-supported vanadia ($V_2O_5/SiO_2$), and transition metal oxide cations such as $PtO^+$, $FeO^+$, and $MnO^+$. Temperatures for these reactions range from about 350° C. to 700° C., with pressures in the range of 5-300 bars.

While 16 such tubes are shown in the reactor illustrated in FIGS. 2a and 2b, it should be understood that this is for illustrative purposes only and a commercial embodiment for practicing this process may utilize a large number of tubes, e.g., as many as 50, 100, 1,000 or more such porous tubes. In various embodiments, such reactors are configured in series or in parallel.

Figure 3A:
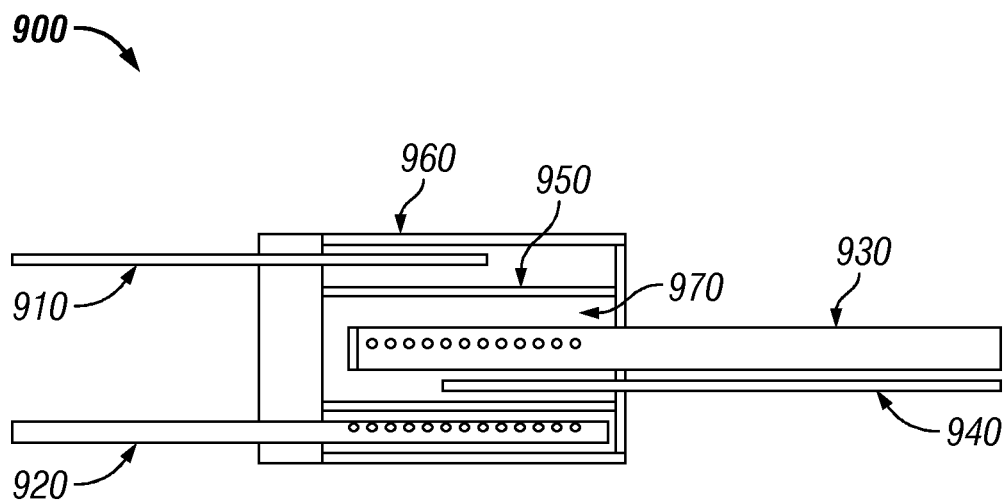
FIG. 3a illustrates a porous metal reactor with a feed gas distribution device in accordance with certain embodiments of this disclosure.

Porous Metal Reactor with Feed Gas Distribution Device. Referring to FIG. 3a, catalyst 970 is first placed within the perforated inner tube 950 and the reactor 900 is sealed by a 1 in NPT (national pipe thread) plug at the base of the reactor. The reactor 900 is placed in a furnace where feed gas (comprising, e.g., methane, steam, carbon oxides, recycle stream) enters through ¼ in tube (920). The outer wall 960 of the reactor 900 transfers heat to the feed gases. Perforations in the feed tube 920 distribute feed gasses in the annular space between the reactor 900 outer shell 960 and the perforated inner shell 950 that holds the catalyst 970. Heated feed gases pass through the catalyst bed 970 and exit through the perforated extraction tube 930. Thermowells 910, 940 measure temperatures of the feed gases and temperatures within the catalyst bed.

In an embodiment, a PMM catalyst comprising a MSR catalyst and a FT catalyst are pressed into a cylinder or other shape as deemed appropriate by one skilled in the art, and placed in a reactor 900 as shown in FIG. 3a. The sintered metal catalyst is shown as 950 in FIG. 3a. The feed gases are methane, steam and hydrogen (no oxygen). Syngas (CO and $H_2$) is produced from methane and then converted to hydrocarbons. In an embodiment, the sintered metal catalyst is formed by pressing and sintering powdered cobalt and nickel into a formed cylinder (such as 950 as shown in FIG. 3a). The thickness of the sintered metal is such that a residence time over/through the catalytic zone is in the range of 0.1 to 5000 microseconds.

Use of PMM catalysts. In an embodiment, the PMM catalyst as described herein is used in a reactor (such as the one illustrated by FIG. 3a) as sintered metal cylinder catalyst. In certain embodiments, the composition of sintered metal catalyst comprises manganese, cobalt, nickel, and iron, an alkali metal, such as sodium, lithium, potassium, rubidium and/or cesium, and zirconium. In certain embodiments, the thickness of sintered metal cylinder is sufficient to maintain its mechanical integrity as well as the range of residence times as stated above. In some embodiments, the pore size is from 1 micron to 500 microns. In some embodiments, the pore size is from 1 micron to 100 microns. In some embodiments, the pore size is from 5 microns to 40 microns. In some embodiments, the pore size is from 5 micron to 20 microns.

In various embodiments, the PMM catalyst as described herein is used to produce various organic compounds, including ethylene, hydrogen, methanol, propylene, ethanol, Dimethyl Ether (DME), aldehydes, and mixed alcohols.

Figure 3B:
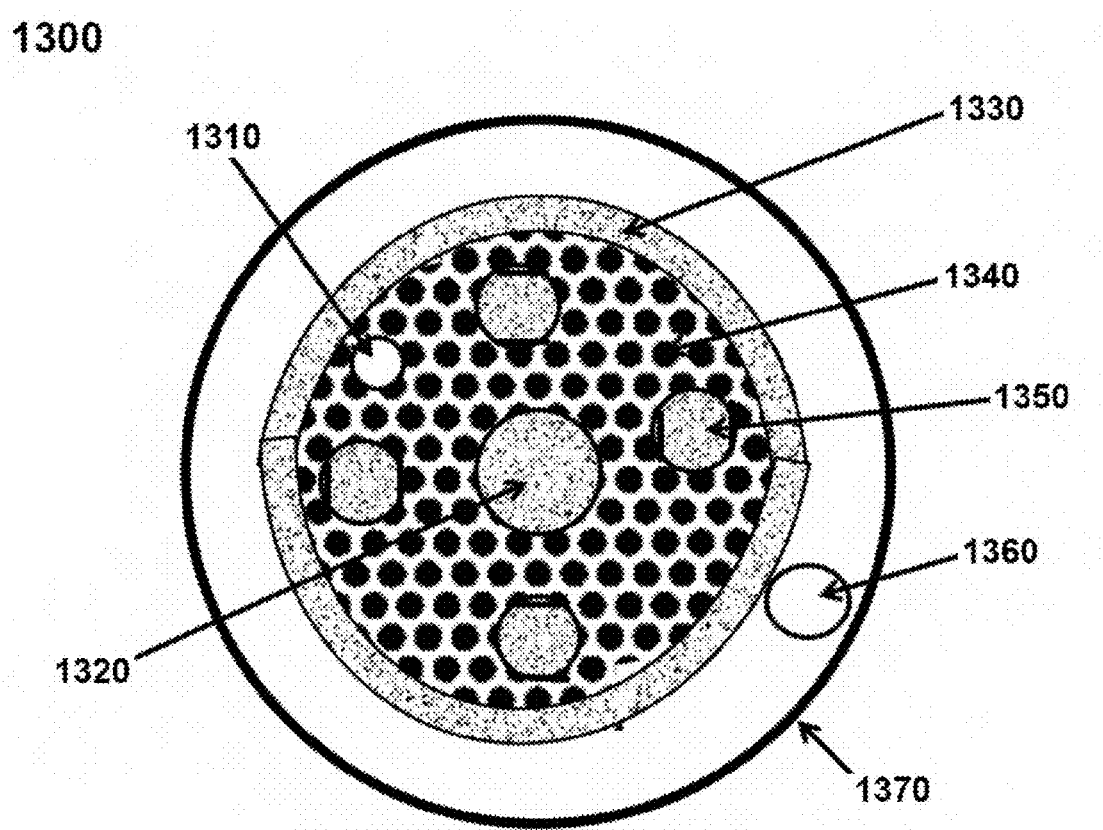

Referring to FIG. 3b, reference numeral 1300 indicates a cross section of the reactor as shown in FIG. 3a. The reactor comprises an outer reactor shell 1370. In an embodiment, methane and steam may enter the reactor 1300 through a gas distribution device or sparger 1320 located at the center of the reactor. The oxygen containing gas enters through four spargers 1350 located towards the outside of the catalyst bed 1340. The oxygen containing gas is restricted from flowing radially either towards the sintered/porous metal distributing the methane and or steam 1320 or towards the outer sintered/porous metal core 1330. The effect is to deliver the oxygen containing gas tangentially to the radially flowing methane/steam gas from the center sparger 1320. The catalyst bed comprises a thermocouple 1310. Reacted gas exits through the outer sintered/porous mental section 1330 and through an outlet tube 1360.

Other reactions for which the reactor design may have utility include hydroformylations, hydrocracking, isodewaxing, isomerizations, dehydrogenations, olefin metathesis, polymerization, paraffin redistribution, alkylbenzene redistribution, and naphtha reforming.

Figure 4:
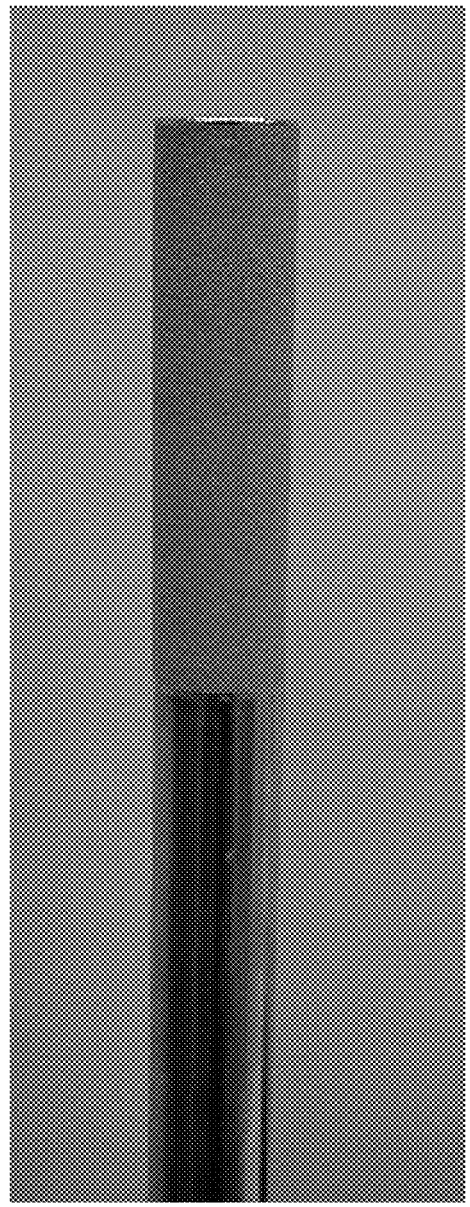
FIG. 4 is a picture of a sintered metal tube suitable for use with methods and systems described in accordance with embodiments of this disclosure.

Porous Metal Reactor with Heat Exchange Device. In an embodiment, a heat exchange device is integrated with a porous metal reactor. In some embodiments, such a heat exchange device is a jacket or sleeve that enclose the catalytic porous/sintered metal tube (as shown in FIG. 4), which provides a passage for a heat exchange medium. In some cases, the heat exchange medium is an inert fluid with respect to the reactions taking place in the reactor. In some cases, the heat exchange medium is a reactant (e.g., steam or water) for the reactions. Whether the heat exchange medium functions to provide or extract heat from the reactor depends on the reaction/operation condition and desired products to be formed. In an embodiment, steam as the heat exchange medium is used to provide heat. In another embodiment, water or steam as the heat exchange medium is used to extract heat.

Figure 5A:
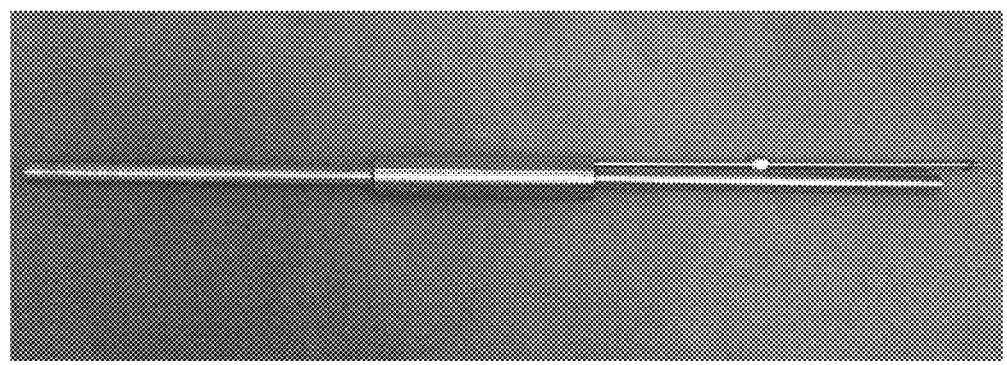
FIGS. 5a and 5b show a catalytic reactor where the catalyst (e.g., a "PMM catalyst", as defined herein) is incorporated in porous or sintered metal inside the reactor in accordance with an embodiment of the disclosure.
Figure 5B:
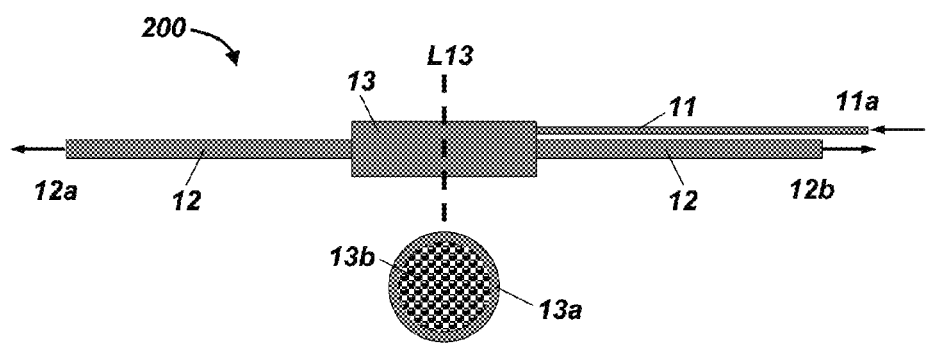

Sintered Metal Reactor. FIGS. 5a and 5b show a catalytic reactor 200 where the catalyst (e.g., a PMM catalyst as described herein) is incorporated in sintered/porous metal 13b inside the reactor. FIG. 5a is an illustration of an exemplary sample reactor; FIG. 5b is a schematic illustration of the sample reactor (top) and a cross-sectional view cut along line L13 of reactor 200 (bottom). Reactor 200 comprises inlet tube 11 with inlet 11a at one end and outlet tubes 12 with outlets 12a and 12b at one end of each tube. The intermediate section 13 of reactor 200 comprises a sintered/porous metal core 13b and an outer shell 13a. Tubes 11 and 12 are fluidly connected with the intermediate section 13 of the reactor so that a feed stream (comprising, for example, steam and methane gas) enters through tube 11 at inlet 11a, passes through sintered/porous metal 13b, and exits through tubes 12 at outlets 12a and 12b.

In some embodiments, a catalyst (e.g., a PMM catalyst) may preferably be embedded in the sintered/porous metal 13b of reactor 200. In some embodiments, the sintered/porous metal 13b is coated with a catalytic material. In some embodiments, sintered/porous metal 13b may be replaced by a ceramic material (e.g., sintered) and a catalyst may preferably be embedded in the ceramic core or coated onto the ceramic core.

In some cases, the sintered/porous metal core or ceramic core is about ¾ inches in diameter and about 6 inches in length. In some cases, the sintered/porous metal core or ceramic core is about ¾ inches in diameter and about 12 inches in length. In some cases, the sintered/porous metal core or ceramic core is about ¾ inches in diameter and about 18 inches in length. In some cases, the sintered/porous metal core or ceramic core is about ¾ inch in diameter and about 24 inches in length. In some embodiments, the loading of catalyst inside the reactor (the sintered/porous metal or ceramic core) is as high as about 200 grams. In some embodiments, the reactor is configured as a shell and tube reactor with oil quenching in one of the tubes to control reaction temperatures.

In some embodiments, (e.g., commercial applications) the diameter of the sintered/porous metal core or ceramic core is larger than ¾ inches. In embodiments, the design of the reactor is related to operational parameters. For example, the length-to-diameter ratio of the reactor is a function of Gas Hourly Space Velocity (GHSV), which is the volume of gas feed per hour per volume of catalyst.

The hydrocarbon feedstock and the steam/oxygen-containing gas are passed over the catalyst, using any of a variety of space velocities. Space velocities for the process, stated as gas hourly space velocity ("GHSV") may range from about 100 to about 30,000 volumes per hour of feed per volume of catalyst. In embodiments, the GHSV range may be from about 200 to about 15,000 NL/L/h. In an embodiment, the gas flow ranged from about 250 to about 5,000 NL/L/h. The effluent stream of product gases emerges from the reactor. Units of gas flow were measured as normal liters of gas per hour per liter of catalyst (NL/L/h).

In various embodiments, reactor 200 is made of type 304 stainless steel due to its high oxidation resistance. In some embodiments, the sintered/porous metal core is also made of type 304 stainless steel. Other high temperature metals may also be used, e.g., titanium. In some embodiments, the reactor core is made of sintered ceramic materials.

In some cases, the average pore size of sintered/porous metal or ceramic 13b in reactor 200 is 20 micron. In some cases, the average pore size of sintered/porous metal or ceramic 13b in reactor 200 is 10 micron. In some cases, the average pore size of sintered/porous metal or ceramic 13b in reactor 200 is 5 micron. In some cases, the average pore size of sintered/porous metal or ceramic 13b in reactor 200 is 3 micron.

In embodiments, the sintered/porous metal or ceramic core is coated with a catalyst.

In embodiments, high volumetric gas is able to pass through reactor 200. For example, steam is able to exit reactor 200 at the outlets with a pressure of 100 psi. With such a high volumetric flow, the gaseous feed stream is well distributed or evenly distributed when the average pore size of sintered/porous metal 13b in reactor 200 is 10 micron or less. In embodiments, high temperature gas is able to pass through reactor 200. For example, steam at a temperature of greater than 850° C. is passed through reactor 10 for the above described OCM and MSR reactions to take place.

Advantages. The reactor designs as described herein allow for a wide range of operating pressures. In some cases, the reactor is able to operate under high pressures (e.g., no less than 100 atm or 10 MPa). In some cases, the reactor is operated under vacuum (e.g., 0.01 inches of Hg absolute pressure). The operating pressure is selected based on the reaction products desired. Furthermore, a large pressure differential is enabled across the sintered metal structure (e.g., two sides of a membrane or the inside and outside of a tube). For example, one side of a sintered metal tube is under high pressure (e.g., 5 atm) and the other side of the tube is under vacuum. The pressure differentials/gradients cause Venturi effects and provide shock quenching or shock cooling as needed. Such pressure differentials enable (1) the desired residence time of the reactants, (2) timely extraction of products, (3) the desired throughput, and (4) suitable heating/cooling capacities.

In various embodiments, the pressure drop across the sintered metal catalytic element(s) is somewhat similar to a nozzle effect in that it creates a high degree of turbulence and the pressure drop causes a reduction in temperature caused by the Joule-Thomson effect or in work producing expansion. In the latter case, the temperature of the process fluid is always reduced hence cooling does not depend on being below the inversion temperature prior to expansion as with the Joule-Kelvin effect. The decrease in temperature takes place when a gas expands through a throttling device as a nozzle. The reduction in temperature may result in rapid quenching of reactions that would not be seen in conventional fixed or fluid bed reactors.

Without being limited by theory, the catalytic porous sintered metal or coated porous ceramic provides for micro channel reactant gas flow at high velocities and high turbulence thus minimizing mass transfer limitations. Furthermore, pushing the feed gas (or reaction mixture) through the sintered/porous metal catalyst creates a shearing force that promotes the formation of reactive intermediate species, such as $CH_3$, $CH_2$, and provides for pressure and temperature changes and reaction quenching. The boundary layer effects/hindrance is reduced/minimized by the use of the catalyst and reactor designs of this disclosure, for example, by the pressure differentials across the catalytic material and/or the short residence time and high flow rate of the gases.

The velocity of the gases is determined by the pressure drop across the porous catalytic surface. This allows for catalytic conversion to syngas and organic compounds with minimal carbon or carbon oxide creation. In embodiments, the localized pressured and temperatures at the point of exit from pores in the sintered metal or porous ceramic results in localized pressures and temperatures that significantly differ from the bulk gas temperatures and pressures. The localized pressures and temperatures are determined by the pressure drop across the sintered metal or porous ceramic as well as the catalytic activity occurring as gases come in contact with catalytic surfaces. In an embodiment, the bulk pressures and/or temperatures are reduced by greater than 10% from what would be expected from kinetics without loss of yield or conversion. In an embodiment, the bulk pressures and temperatures may be reduced by 50% from what would be expected from kinetics without loss of yield or conversion.

In embodiments, a reducing atmosphere of feed gases over the PMM catalyst is created by addition of hydrogen to the feed gases. In embodiments a reducing atmosphere over the PMM catalyst is created by generation of hydrogen by means of one of the mechanisms discussed herein.

In embodiments, the PMM catalyst comprises MSR, SG and FT catalysts such that temperature equilibrium is achieved between exothermic and endothermic reactions with minimal external heat exchange required.

In embodiments, the composition of feed gases is optimized to minimize carbon oxide creation. In some embodiments, the partial pressure of each feed gas component ($CO$, $H_2O$, $CO_2$, $CH_4$ and $H_2$) is controlled to change the conversion and yields of the reaction products. For example, as the inlet partial pressures of $CO_2$ and $H_2$ are increased, the CO conversions decrease. In the cases of increasing $H_2O$ partial pressure or decreasing CO partial pressure, the CO conversion increases.

In certain embodiments, different PMM catalysts are employed in the two different locations within the porous metal reactor. For example, iron-based catalysts may be used for high temperature (300° C. to 900° C.) and copper-based for low temperature (150° C. to 300° C.) water gas shift reactions. The exact composition of these catalysts may vary according to their specific applications and their accompanying supports (i.e. $ZnO/Al_2O_3$, $CeO_2$, etc.). In an embodiment, the SG catalyst comprises nickel as the active component for promoting syngas production due to the resistance to sintering at elevated operating temperatures.

In certain embodiments, the PMM catalyst of this disclosure comprising OCM catalyst has minimal coking of the catalyst. In certain embodiments, the presence of steam reforming catalyst eliminates the need of an oxygen source, thus reducing equipment and operation costs. Furthermore, in certain embodiments, undesirable byproducts, such as carbon oxides, are minimized.

Another advantage of the catalysts and processes of this disclosure is that the resulting product mixture favors the production of hydrogen; i.e., hydrogen is a product of the present process and/or more hydrogen is combined with carbon in the final products as hydrocarbons than in conventional processes.

In some embodiments, the catalyst is incorporated into a reactor comprising a sintered/porous metal sparger (or porous membrane) (see FIGS. 1a and 1b) to distribute reactant gases evenly throughout the catalyst bed. In some cases, the porous membrane is constructed of ceramic materials, e.g., alumina, silica, titania, aluminosilicate(s), as are known in the art. In some cases, the porous membrane comprises sintered metal, e.g., titanium, stainless steel, and the like. In some cases, the porous membrane comprises porous metal.

In some cases, the porous membrane comprises catalytic materials that promote reactions. In some embodiments, the porous membrane is coated with catalytic metals by means of vapor deposition.

In an embodiment, the reaction is carried out at higher than conventional temperatures with minimum carbonation and/or coking. In some embodiments, the reaction takes place at pressures higher than the atmospheric pressure. In some embodiments, the reaction takes place at pressures lower than the atmospheric pressure. In some cases, the reaction takes place at a pressure that is below atmospheric pressure or at absolute pressure of about 10 kpa absolute.

In embodiments, the method of this disclosure has higher yields compared to conventional methods that produce organic compounds. In some cases, the single pass yield of organic compounds is above 75%. In some cases, the single pass yield of organic compounds is about 75%. In some cases, the single pass yield of organic compounds is 70%-75%. In some cases, the single pass yield of organic compounds is 60%-75%. In some cases, the single pass yield of organic compounds is 50%-75%. In some cases, the single pass yield of organic compounds is 40%-75%. In some cases, the single pass yield of organic compounds is 30%-75%.

Mechanisms. The mechanism disclosed herein is to produce organic compounds (e.g., alcohols and hydrocarbons) from simple alkanes, primarily methane. As used herein, the term "organic compounds" refers to compounds such as, but not limited to, ethylene, ethane, propylene, propane, butane, butene, heptane, hexane, heptene, octane, and all other linear and cyclic hydrocarbons where two or more carbons are present. "Organic compounds" also refers to alcohols, esters, and other oxygen containing organic compounds. Methanol is a single carbon molecule that is also included herein as an alcohol that is produced by the present disclosure.

The mechanism disclosed herein to produce organic compounds is by means of two or more chemical reactions occurring in a single reactor. Under normal operation conditions, molecular oxygen in the feed gas is not required.

In an embodiment, a first chemical reaction involving water-gas shift reactions utilizes a reducing atmosphere and reduced catalyst (i.e. metal catalyst not containing oxygen) to produce syngas (CO and $H_2$) from steam and methane. The second chemical reaction in the process involves what is commonly called the Fischer Tropsch reaction where syngas is converted to organic compounds and/or simple alcohols. The methods and systems of disclosure are able to produce syngas and convert it into organic compounds (e.g., hydrocarbons and simple alcohols) within a single reactor by means of the reactor designs and catalysts as described herein.

In another embodiment, oxidative or non-oxidative dehydrogenation of methane takes place first to produce reactive species that then form organic compounds. Higher carbon number hydrocarbons may be formed with the addition of chain growing FT-type catalysts.

Without being limited by theory, the combination of OCM catalyst and MSR catalyst may produce organic compounds due to production of mobile species, i.e., adsorbed oxygen or adsorbed OH produced under the action of MSR catalyst which migrate from the active sites of MSR catalyst to the OCM catalyst to create active sites for producing an adsorbed methyl species, which desorbs to produce the methyl radical. The methyl radical or even the adsorbed methyl species combines at the reaction temperatures to form adsorbed ethane which desorbs to produce ethane. The methyl radical in the gas phase may also combine to produce ethane, which will dehydrogenate to ethylene.

In embodiments, the MSR promoting catalyst component of the PMM catalyst creates syngas by means of reactions that may be depicted as follows:

$$CH_4 + H_2O \leftrightarrow CO + 3H_2 \Delta H = +206 \text{ kJ/mol}$$

$$CO + H_2O \leftrightarrow CO_2 + H_2 \Delta H = -41 \text{ kJ/mol}$$

The $CO + H_2O \leftrightarrow CO_2 + H_2$ reaction is generally referred to as the water-gas-shift (WGS) reaction. These reactions are generally carried out in conventional reactors in the temperature range of 300° C. to 900° C. in multiple adiabatic stages with inter-stage cooling to obtain higher conversions overall. Lower temperatures are generally desirable to minimize carbon formation with steam to carbon ratios ranging from about 2 to 5.

In embodiments, the SG catalyst component of the PMM catalyst creates mainly syngas by means of the following reactions;

$$CH_4 + CO_2 \leftrightarrow 2CO + 2H_2 \Delta H = +165 \text{ kJ/mol}$$

$$CH_4 \leftrightarrow C + 2H_2 \Delta H = +75 \text{ kJ/mol}$$

$$2CH_4 + H_2 + \tfrac{1}{2}H_2O \rightarrow 3H_2 + C_2H_4 + \tfrac{1}{2}H_2O$$

In an embodiment, a PMM catalyst comprises a MSR catalyst and a FT catalyst. In such cases, methane is converted to CO via MSR reaction; the MSR catalyst is doped with a Fischer-Tropsch catalyst (such as cobalt, iron and/or manganese). The mechanism is that the MSR catalyst doped with a FT catalyst performs the reforming steps by first making CO from the MSR reaction and then converts CO to hydrocarbons.

In some embodiments, under the action of the PMM catalyst, the following reactions may take place:

$$2CH_4 + H_2 + \tfrac{1}{2}H_2O \rightarrow 3H_2 C_2H_4 + \tfrac{1}{2}H_2O$$

$$CH_4 + H_2O \rightarrow CO + 3H_2 [\Delta H = +206 \text{ kJ mol}^{-1}]$$

$$CO + H_2O \rightarrow CO_2 + H_2 [\Delta H = -41 \text{ kJ mol}^{-1}]$$

$$CH_4 + 2H_2O \rightarrow CO_2 + 4H_2 [\Delta H = +165 \text{ kJ mol}^{-1}]$$

$$CH_4 + CO_2 \leftrightarrows 2CO + 2H_2 [\Delta H = +247 \text{ kJ mol}^{-1}]$$

$$CH_4 \leftrightarrows C + 2H_2 [\Delta H = +75 \text{ kJ mol}^{-1}]$$

In some embodiments, metals present in the PMM catalyst also produce alcohols through the following reactions:

$$CO + 2H_2 \leftrightarrow CH_3OH [\Delta H = -90.8 \text{ kJ mol}^{-1}]$$

$$CO_2 + 3H_2 \leftrightarrow CH_3OH + H_2O [\Delta H = -49.6 \text{ kJ mol}^{-1}]$$

While preferred embodiments of the invention have been shown and described, modifications thereof may be made by one skilled in the art without departing from the spirit and teachings of the invention. The embodiments described herein are some only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide some, procedural or other details supplementary to those set forth herein.

What is claimed is:

1. A method comprising utilizing a reactor comprising
   a housing;
   an inlet tube having a section with perforations along its length, wherein said inlet tube section is disposed at least in part within said reactor housing;
   an outlet tube having a section with perforations along its length, wherein said outlet tube section is disposed at least in part within said reactor housing; and
   at least one cylinder comprising a sintered metal disposed at least in part within the reactor housing, wherein said sintered metal is catalytically active and wherein the residence time through the sintered metal is in the range of from 0.1 to 5000 microseconds;
to produce organic compounds from a feed stream comprising methane and steam and optionally hydrogen.

2. The method of claim 1 wherein said sintered metal comprises a porous metallic multifunctional (PMM) catalyst comprising
   (a) a catalyst that promotes the oxidative coupling of methane (OCM) and a methane steam reforming (MSR) catalyst, wherein said catalyst composition causes oxidative dehydrogenation to form reactive species and oligomerization of said reactive species to produce organic compounds; Or
   (b) a catalyst that promotes syngas generation (SG) and a Fischer-Tropsch (FT) catalyst wherein said catalyst composition causes non-oxidative dehydrogenation to form reactive species and oligomerization of said reactive species to produce organic compounds; or
   (c) an SG catalyst, an MSR catalyst, and an FT catalyst wherein said catalyst composition causes non-oxidative dehydrogenation to form reactive species and oligomerization of said reactive species to produce organic compounds; or
   (d) an FT catalyst and an MSR catalyst wherein said catalyst composition causes reforming reactions and chain growing reactions to produce organic compounds.

3. The method of claim 1 wherein said reactor comprises two or more cylinders, and optionally wherein said at least one cylinder is concentric with respect to the reactor housing.

4. A method comprising utilizing a reactor system comprising a first reactor and a second reactor, wherein an outlet of said first reactor is fluidly connected to an inlet of said second reactor, wherein each of said reactors comprises a housing; an inlet tube having a section with perforations along its length, wherein said inlet tube section is disposed at least in part within said reactor housing; an outlet tube having a section with perforations along its length, wherein said outlet tube section is disposed at least in part within said reactor housing; and at least one cylinder comprising a sintered metal disposed at least in part within the reactor housing, wherein said sintered metal is catalytically active and wherein the residence time through the sintered metal is in the range of from 0.1 to 5000 microseconds;

to produce organic compounds from a feed stream comprising methane and steam and optionally hydrogen.

5. The method of claim 1 wherein the reactor is configured to have a pressure differential across the sintered metal in operation.

6. A method of performing a reaction comprising utilizing a shell and tube reactor comprising a shell and a multiplicity of sintered metal tubes contained within said shell, wherein said sintered metal tubes are catalytically active and wherein the residence time through the sintered metal is in the range of from 0.1 to 5000 microseconds;

an inlet and an outlet for a heat exchange medium; and an inlet for reactants and an outlet for products;

to convert reactants to products.

7. The method of claim 4 wherein the reactor system further comprises an inter-reactor gas injector, and optionally inter-reactor heat addition or heat removal.

8. The method of claim 6 wherein said sintered metal tubes comprise a porous metallic multifunctional (PMM) catalyst comprising (a) a catalyst that promotes the oxidative coupling of methane (OCM) and a methane steam reforming (MSR) catalyst, wherein said catalyst composition causes oxidative dehydrogenation to form reactive species and oligomerization of said reactive species to produce organic compounds; or (b) a catalyst that promotes syngas generation (SG) and a Fischer-Tropsch (FT) catalyst wherein said catalyst composition causes non-oxidative dehydrogenation to form reactive species and oligomerization of said reactive species to produce organic compounds; or (c) an SG catalyst, an MSR catalyst, and an FT catalyst wherein said catalyst composition causes non-oxidative dehydrogenation to form reactive species and oligomerization of said reactive species to produce organic compounds; or (d) an FT catalyst and an MSR catalyst wherein said catalyst composition causes reforming reactions and chain growing reactions to produce organic compounds.

9. The method of claim 6 wherein the pressure of the reactants is higher than the pressure of the heat exchange medium.

* * * * *